United States Patent [19]

Pedersen et al.

[11] Patent Number: 4,511,674
[45] Date of Patent: Apr. 16, 1985

[54] PROCESS AND CATALYST FOR THE PREPARATION OF A GAS MIXTURE HAVING A HIGH CONTENT OF $C_2$-HYDROCARBONS

[75] Inventors: Karsten Pedersen, Birkerod; Jens R. Rostrup-Nielsen, Virum; Ib Greve H. Jørgensen, Bloustrod, all of Denmark

[73] Assignee: Haldor Topsøe A/S, Lyngby, Denmark

[21] Appl. No.: 434,493

[22] Filed: Oct. 15, 1982

Related U.S. Application Data

[63] Continuation-in-part of Ser. No. 215,546, Dec. 11, 1980, abandoned.

[30] Foreign Application Priority Data

Dec. 18, 1979 [DK] Denmark .......................... 5395/79

[51] Int. Cl.$^3$ .............................................. C07C 1/04
[52] U.S. Cl. .................................... 518/714; 518/715; 518/721; 518/717
[58] Field of Search .................... 518/714, 715, 721

[56] References Cited

U.S. PATENT DOCUMENTS

| | | |
|---|---|---|
| 2,960,518 | 11/1960 | Peters . |
| 3,730,694 | 5/1973 | Wanderlich . |
| 4,039,302 | 8/1977 | Khera . |
| 4,151,190 | 4/1979 | Murchism et al. . |
| 4,177,202 | 12/1979 | Chang et al. . |
| 4,320,030 | 3/1982 | Happel .......................... 518/714 |

FOREIGN PATENT DOCUMENTS

| | | | |
|---|---|---|---|
| 2536488 | 12/1976 | Fed. Rep. of Germany . | |
| 379335 | 8/1932 | United Kingdom | ................ 518/714 |

Primary Examiner—Howard T. Mars
Attorney, Agent, or Firm—Dennis P. Clarke

[57] ABSTRACT

A gas mixture rich in ethan and/or ethylene is prepared by the conversion of a synthesis gas mixture containing hydrogen, carbon oxides and, optionally, other gases in the presence of one or more gaseous sulphur compounds, in an amount of at least 10 ppm by volume, preferably at least 200 ppm, calculated as $H_2S$, utilizing a catalyst consisting of one or more metals of group V-B and/or VI-B of the Periodic Table of Elements, preferably molybdenum and/or vanadium, together with one or more iron group metals each metal being in the form of free metal, oxide, or sulphide, the catalyst being supported on a porous, refractory oxidic support containing titanium dioxide.

There is achieved a high activity and notably a high selectivity for the formation of ethane/ethylene, small amounts of propane, not insignificant amounts of methane and almost full suppression of the formation of higher hydrocarbons.

The invention also relates to the catalyst prepared by impregnation or coprecipitation techniques.

2 Claims, No Drawings

PROCESS AND CATALYST FOR THE PREPARATION OF A GAS MIXTURE HAVING A HIGH CONTENT OF C₂-HYDROCARBONS

This is a continuation-in-part of copending application Ser. No. 215,546 filed on Dec. 11, 1980, now abandoned.

FIELD OF THE INVENTION

The present invention relates to a process for the preparation of a gas mixture having a high content of $C_2$-hydrocarbons, i.e., ethane and ethylene (ethene), by the catalytic conversion of a synthesis gas containing hydrogen and carbon oxides and, optionally, other gases.

BACKGROUND OF THE INVENTION

Synthesis gas is conventionally prepared by gasification, usually steam treatment, of coal or heavy petroleum fractions according to the reaction:

$$C + H_2O \rightarrow CO + H_2 \tag{1}$$

accompanied, however, by side reactions forming carbon dioxide and small amounts of methane. When petroleum fractions are gasified the amount of hydrogen in the synthesis gas is higher than when coal is gasified. Some coal gasification processes involve the formation of higher amounts of methane, other hydrocarbons, tar, etc. During gasification oxygen is normally added in order to render the gasification self-supplying with heat.

By various reactions the synthesis gas may be converted into methane. In recent years such reactions have become increasingly important from the standpoint of preparing substitute natural gas (SNG), special gas transport systems and as a source of energy. Typical reactions include:

$$CO + 3H_2 \rightleftharpoons CH_4 + H_2O \tag{2}$$

$$2CO + 2H_2 \rightleftharpoons CH_4 + CO_2 \tag{3}$$

The carbon dioxide may also be converted with hydrogen into methane:

$$CO_2 + 4H_2 \rightleftharpoons CH_4 + 2H_2O \tag{4}$$

The so-called shift reaction causes an equilibrium between carbon monoxide and carbon dioxide:

$$CO + H_2O \rightleftharpoons CO_2 + H_2 \tag{5}$$

Moreover, synthesis gas may be converted by the Fischer-Tropsch synthesis (also called the FT synthesis) into methane and higher hydrocarbons, particularly paraffins and olefins, but possibly even into aromatic compounds:

$$2nCO + (n+1)H_2 \longrightarrow C_nH_{2n+2} + nCO_2 \tag{6}$$
(paraffin reaction)

$$2nCO + nH_2 \longrightarrow C_nH_{2n} + nCO_2 \tag{7}$$
(olefin reaction), and possibly also $$nCO + 2nH_2 \longrightarrow C_nH_{2n} + nH_2O \tag{8}$$
(olefin reaction).

The FT-synthesis is used for the production of motor fuel and other liquid fuels. It might also be of interest for preparing $C_2$-hydrocarbons but is not very suitable therefor because of its low selectivity. The $C_2$-olefin ethylene is a very expedient starting material for many organic syntheses so that petrochemical products thereby can be formed from lignite, coal and heavy petroleum fractions.

In contradistinction to the FT synthesis the invention especially aims at an efficient conversion of synthesis gas into $C_2$-hydrocarbons and in this connection it is observed that it is not essential whether ethane or ethylene is directly prepared because ethane may be cracked to ethylene at a high efficiency by well-known technology.

The FT synthesis is a kind of polymerization reaction in which the yield structure follows the so-called Flory distribution (see for instance G. Henrici-Olive et al, Angew. Chemie. 15, 136, 1976, and H. Schultz et al, Fuel Proc. Technol. 1, 31, 1977), a theoretical distribution of the various chain lengths which can be deduced mathematically from simplified kinetic assumptions. It can be shown that the Flory distribution theoretically may give a maximum yield of about 27% by weight of ethane and/or ethylene, calculated as the carbon in the hydrocarbons formed by the synthesis. In practice the yield of $C_2$-hydrocarbons in FT synthesis is almost always far below that expected according to the Flory distribution and only in a few cases has it been possible, under special circumstances, to obtain a $C_2$-hydrocarbon yield corresponding to or above that according to the Flory distribution. Moreover, it has not hitherto in FT syntheses been possible to avoid the formation of hydrocarbons having more than 4 carbon atoms.

Nearly all metals and to a considerable degree even oxides and hydroxides thereof have been proposed as catalysts for FT synthesis, frequently on support substances. There is often used one or more heavy metals with a promoter of an alkali metal oxide. The most important of the industrially employed FT catalyst metals are iron and cobalt. It is a drawback that they are also catalysts for the conversion of carbon monoxide into free carbon and carbon dioxide by the exothermal Boudouard reaction:

$$2CO \rightarrow C + CO_2 \tag{9}$$

The carbon formation causes irreversible damage to the catalyst and the reaction therefore imposes limitations on the usable process parameters. Moreover, the steam formed by the synthesis under some circumstances may cause the oxidation of iron catalysts, which totally or partly deactivate them. Other FT catalyst metals tolerate oxidation without concomittant deactivation. All known FT catalysts are more or less sensitive to sulphur poisoning and therefore the synthesis gas must be carefully rid of sulphur compounds before being subjected to FT synthesis. Many FT catalysts are sulphided but nevertheless are sensitive to sulphur poisoning; the sulphided catalysts containing only very small amounts of sulphur. The purification of the synthesis gas of sulphur compounds is a substantial economic burden on the FT process. In the majority of cases the sulphur content in the synthesis gas must be kept below 0.1 ppm, calculated as $H_2S$, whether it is to be methanated or used for FT synthesis. Dalla Betta et al (J. Catal. 37, 449, 1975) showed that 10 ppm of $H_2S$ in the synthesis gas stream at 400° C. destroyed $Ru/Al_2O_3, Ni/Al_2O_3$ or Raney nickel catalysts.

Shultz et al (U.S. Dept. of the Interior, Bureau of Mines Report 6974, 1967) showed that ruthenium and molybdenum are promising catalysts for hydrocarbon synthesis whereas tungsten and noble metals other than ruthenium could be left out of consideration. Molybdenum, the catalytic activity of which is not on a par with that of the metals of the iron group, has since been investigated thoroughly and it is known that methanation and FT catalysts based on molybdenum are more resistant to sulphur poisoning than the metals of the iron group. Mills et al state (Catal. Rev. 8(2), 159–210, 1973) that catalysts of molybdenum oxides on $Al_2O_3$ or other support had a rather high activity with respect to conversion of $H_2/CO$ and a selectivity for methane formation of 80–94% and for $C_2$-hydrocarbon formation of 6–16% under certain circumstances. By sulphiding to molybdenum sulphides the activity decreased, which could be compensated for by pressure increase, and the yield of methane became about 94% and of $C_2$-hydrocarbons 5.9%. By the addition of $H_2S$ to the synthesis feed gas the activity decreased (sulphur poisoning) and at the same time the selectivity changed with a drop in the methane yield at 64.6% and the $C_2$ yield at 4.1% whereas the formation of $C_3+C_4$ hydrocarbons increased at 29.4%. The effect of $H_2S$ on the catalyst was reversible and temporary; i.e., its removal from the feed gas stream resulted in an increase in selectivity.

Madon and Shaw state in a review in Catal. Rev.-Sci. Eng. 15(1), 69–106 (1977) that FT catalysts based on metallic, oxidic or surface sulphided molybdenum do have decreased activity in the presence of $H_2S$ in the synthesis gas but that the effect is temporary and reversible so that the original activity of the catalyst returns when the sulphur is removed from the feed gas; in this respect molybdenum contrasts strongly with nickel and ruthenium based catalysts in which the poisoning can be considered definitive and lasting because of the strong affinity of these catalysts to sulphur and because the chemisorbed sulphur is in equilibrium with very low concentrations of $H_2S$. Madon and Shaw also call attention to the fact that a catalyst based on molybdenum sulphides is strongly selective for methane formation (more than 90% of the carbon converted into hydrocarbons is converted into methane), whereas the presence of larger amounts of $H_2S$ in the feed gas causes a change so that nearly 30% is converted into $C_{3-4}$ hydrocarbons and only about 60% into methane. The amount of $C_2$-hydrocarbons produced is very small. From South Africa patent specification No. 766,137 it is known that vanadium-based catalysts for methane formation are rather sulphur resistant. Vanadium has a considerable selectivity for methane formation but it is stated in the said specification that by promotion of a $V_2O_3$-catalyst on a support of $Al_2O_3$ with $MoO_3$ a rather high yield of ethane can be obtained along with a decrease of the methane yields at concentrations of $H_2S$ which are rather low but still much higher than those tolerated by nickel catalysts.

U.S. Pat. No. 4,151,190 relates to a process for optimizing the yield of saturated and unsaturated $C_2$–$C_4$-hydrocarbons. There is used a catalyst of 1–95% by weight of metal, oxide, or sulphide of Re, Ru, Pt or preferably Mo or W, 0.5–50% by weight of hydroxide, oxide, or salt of an alkali or alkaline earth metal and at least 1% support, preferably carbon or alumina. The alkaline component and the support enhance the formation of $C_2$–$C_4$-hydrocarbons and the Examples of the specification show that up to 40.5% of the hydrocarbons formed may be $C_2$-hydrocarbons. This result was obtained with a catalyst of tungsten trioxide and potassium oxide and a support of carbon. The Examples of the specification also show that even small amounts of gaseous sulphur compounds in the feed gas stream alter the selectivity of the catalyst in favor of a high methane formation and usually decrease its activity strongly. By removing the sulphur from the feed gas stream the original activity and selectivity may be recovered.

Accordingly, there is still a need in the art for a process and particularly a catalyst which, in Fischer-Tropsch syntheses, may give a high yield of ethane and/or ethylene and at the same time has a good activity in the presence of sulphur compounds in the synthesis gas thereby enabling the saving of the costs involved in sulphur removal.

It has now surprisingly been found that a small class of catalyst metals, viz. groups V-B and VI-B in the Periodic Table of Elements, in combination with metals of the iron group and supported on certain support materials is sulphur tolerant, retains a high degree of activity in the presence of sulphur and can give high yields of $C_2$-hydrocarbons.

Prior to describing the catalyst and process in detail, it should be mentioned that catalysts of a similar general type are known for various other purposes. Thus, Swedish patent specification No. 395,676 discloses a catalyst for the shift reaction (5) consisting of an alumina support impregnated with nickel and/or cobalt sulphide, aluminum sulphide and molybdenum sulphide. Swedish patent specification No. 407,680 discloses a process for the oxidation of methanol to formaldehyde using a catalyst obtained by the coprecipitation of dissolved molybdenum and iron compounds, admixing with titanium dioxide, and subsequent drying and calcination. U.S. Pat. No. 2,830,960 discloses a catalyst containing oxides of cobalt and molybdenum on activated alumina supports useful for hydrocatalytic desulphurization of hydrocarbons. U.S. Pat. No. 3,132,111 discloses a catalyst for such hydrotreating processes as hydrodesulfurization, hydrofinishing, and hydrocracking of normally liquid petroleum feedstocks. The catalyst consists of an alumina support containing a metal component of the iron transition group, metals from the fifth and sixth periods of group VI-B and vanadium, for instance a $CoO.MoO_3.Al_2O_3$ catalyst. U.S. Pat. No. 3,242,101 discloses a nickel-molybdenum-alumina hydrocarbon conversion catalyst, showing especially high activity for desulfurization, denitrogenation and hydrogenation of olefins and aromatics. Finally, U.S. Pat. No. 4,128,505 discloses a catalyst for hydrocarbon desulfurization, denitrogenation and aromatics saturation, which catalyst consists of coprecipitated titania and zirconia, the coprecipitate having associated therewith a mixture of (1) cobalt as metal, oxide or sulphide, and (2) molybdenum as oxide or sulphide.

Based on this background it is surprising that the process and catalysts described more fully hereinafter are active and highly selective for converting synthesis gas containing sulfur compounds into $C_2$-hydrocarbons.

SUMMARY OF THE INVENTION

In accordance with the present invention, there is provided a process for the preparation of a gas mixture having a high content of ethane and/or ethylene by the catalytic conversion at a pressure of 1-500 bar and a temperature of 200°-600° of a feed gas (synthesis gas) containing hydrogen and carbon oxide and optionally other gases, in which process the feed gas contains or is caused to contain, at least 10 ppm by volume (calculated as $H_2S$) of one or more gaseous sulphur compounds and in which the conversion takes place in the presence of at least one metal of group V-B and/or VI-B in the Periodic Table of Elements, in the form of free metal, oxide, or sulphide, and at least one metal of the iron group in the form of free metal, oxide, or sulphide, on a porous oxidic ceramic support containing titania.

It has been found that, by operating according to the present invention, it is possible to obtain a decisive deviation from the Flory distribution and to obtain the formation of ethane and/or ethylene as the predominant hydrocarbon component of the product gas with almost complete suppression of the formation of hydrocarbons containing more than 3 carbon atoms. As a rule there is formed considerable amounts of ethane and small amounts of $C_3$-hydrocarbons, mainly propane. The propane will be cracked together with ethane to ethylene in accordance with conventional practice in the art. The methane or part thereof may be used as an energy source for the cracking of ethane and propane when the product gas is to be used as starting material in petrochemical industries, and the remainder may, for example, be used as fuel, e.g., as substitute natural gas.

The invention also provides a catalyst for the process described. The catalyst consists of (1) at least one metal of groups V-B and/or VI-B of the Periodic Table of Elements in the form of free metal, salt, oxide, or sulphide, and (2) at least one metal of the iron group in the form of free metal, salt, oxide, or sulphide, on (3) a porous, oxidic ceramic support containing titania.

DETAILED DESCRIPTION OF SPECIFIC EMBODIMENTS

As feed gas it is possible to use synthesis gas as described and having varying proportions of hydrogen and carbon oxides and which optionally also contain other gases such as steam, methane and small amounts of other hydrocarbons; a content of nitrogen and the inert gases, e.g., from combustion air, will do no harm. The volume ratio of hydrogen to carbon monoxide will typically vary form about 0.4:1 to about 3:1, preferably close to equal parts of hydrogen and carbon monoxide as is obtained according to the above equation (1). It is a special advantage of the process that it can be carried out at such low relative amounts of hydrogen because (1) labor and costs involved in enriching the synthesis gas feeds of prior art methods with hydrogen are saved, and (2) it is inherently closer to a stoichiometric ratio corresponding to longer carbon chains than $C_1$. In known methanations and FT-synthesis it is usually necessary to have a higher volume ratio (mole ratio) $H_2/CO$ than 1 in order to avoid formation of free carbon on the catalyst according to the Boudouard reaction (9) and consequent destruction of the catalyst. Formation of carbon causes irreversible damage to the catalyst and the Boudouard reaction therefore imposes limitations on the usable process parameters. It has been found that the addition of sulphur suppresses the carbon formation and also the formation of graphite (so-called "gum-forming" reaction) which often precedes the carbon formation and is a polymerization to form long carbon chains having a low content of hydrogen; see J. R. Rostrup-Nielsen and Karsten Pedersen, J. Catal. 59, 375, 1979.

It is important that sulphur is present in the feed gas in the form of one or more gaseous sulphur compounds because the sulphur establishes the especially catalytically active sulphide phase of the catalyst metals. The amount of sulphur is not overly critical since the amount of sulphur needed to preserve the sulphide phases is very low compared to the amount of gas reacted. The minimum amount of sulphur, calculated as $H_2S$, is about 10 ppm, calculated on the volume of the feed gas. In most cases the practical minimum amount will be 200 ppm by volume and very frequently the content will be of the order of magnitude 1000 or 1000-3000 ppm by volume, calculated as $H_2S$. The amount will rarely be above about 2% by volume of sulphur, calculated as $H_2S$. This in practice means that it is not at all necessary to remove sulphur from the synthesis gas or from the raw materials such as coal or heavy oil gasified to synthesis gas. The amount of sulphur is thus not overly critical and neither is the type of gaseous sulphur compound. As examples may be mentioned hydrogen sulphide, sulphur dioxide, carbonyl sulphide, carbon disulphide, mercaptans, thioethers, disulphides and thiophene. It is not known why the presence of sulphur in such high amounts gives results other than where sulfur is present in known FT synthesis. It is assumed that, in the process according to the invention, a fundamentally different reaction mechanism is involved than the polymerization causing the Flory distribution in the known FT syntheses wherein low amounts of $C_2$-hydrocarbons are present in the distribution of products. There may, however, be reasons to assume that sulphur-containing carbon compounds, particularly carbon disulphide and carbonyl sulphide occur as intermediates.

The process may be operated over a wide pressure range and the working pressure chosen is determined to a high degree by such factors as the actual pressure of the available synthesis gas and the pressure desired for the product gas. As will be seen from Example 3 hereinbelow, increased pressure will favor the formation of ethane and propane and suppress the formation of olefins and higher hydrocarbons, whereas a low pressure will favor formation of methane. Increased pressure also increases the activity and thus allows a higher space velocity (SV, i.e., the velocity of the flow measured as volumes of gas per amount of catalyst per unit time). By balancing the various considerations the process usually will be operated at 1-500 bar, particularly 15-150 bar and preferably 20-100 bar, e.g., about 80 bar which is a frequently occurring coal gasification pressure.

The temperature of the reaction may vary within wide limits and will normally be within the range 200°-600° C. A high temperature within the range stated will favor the formation of methane, a lower temperature the formation of ethane and/or ethylene as will be seen from Example 2 hereinbelow. It is therefore preferred to keep the temperature as low as is consistent with a reasonable rate of reaction. Most often there will be used a temperature in the range 270°-400° C., preferably 300°-350° C.

The catalyst in the process according to the invention contains at least one metal of group V-B (vanadium, niobium and tantalum) and/or VI-B (chromium, molybdenum and tungsten) in the Periodic Table. It is surprising that molybdenum and vanadium are valuable for forming of $C_2$-hydrocarbons since, as shown hereinabove, they are considered in the art to be mainly methane-producing catalysts. The reason probably is that groups V-B and/or groups VI-B metals are accompanied by a catalyst metal of the iron group (iron, cobalt, nickel) which favor $C_2$-formation at the expense of methane.

The metals in the fresh catalyst are present in the form of free metal, salt, oxide or sulphide. It is not overly important which form is used since it must be assumed that the salt and oxide, because of the presence of the hydrogen in the synthesis gas, are reduced to free metal and that the free metal is sulphided under the influence of the sulphur to sulphide, e.g., mono-, di- or polysulphides and/or oxysulphides, whereby the metals in the reaction mixture are always present in the catalyst as sulphides. The amount of catalyst metals in the catalyst and the ratio of the two metals or classes of metals (metal of group V-B or VI-B on one hand and of the iron group on the other hand) is not overly critical. Conviently the content of metal(s) of group V-B and/or VI-B will be 1–40%, calculated as oxide on the total weight of support plus metal (oxide); and 0.5–10% of metal of the iron group, which will normally constitute a smaller amount than the metals first mentioned, calculated in the same manner. A particularly high selectivity for $C_2$-hydrocarbons combined with a high activity is possessed by molybdenum and vanadium, each combined with iron or cobalt.

Optionally an alkali metal or alkaline earth metal compound may be present on the catalyst as promoter but preferably the catalyst does not need to contain such promoters since they tend to favor methane production.

It has been found that a good activity and selectivity for ethane/ethylene is obtained when $TiO_2$ or $TiO_2/Al_2O_3$ are utilized as support materials for the catalyst of the present invention. Titania has been found to yield the highest activity and is the preferred carrier material.

The best results with respect to a high selectivity for $C_2$ and a high activity are obtained if the catalyst is molybdenum sulphide and cobalt sulphide supported on a carrier of porous titanium dioxide.

The reaction is conducted substantially in a manner which is well-known per se in Fischer-Tropsch and methanation reactions. Thus, the catalyst is placed as a fixed bed or fluid bed in a reactor into which the synthesis gas is passed via suitable lines, optionally in a preheated condition. The reaction is exothermal and it is therefore necessary to limit the increase of temperature in the reactor, which can be done in various ways. The reactor may be an adiabactic reactor where part of the product gas is recycled and mixed with the feed gas, which is thereby diluted with an ensuing limitation of the increase in temperature. Advantageously, the reactor may be a cooled reactor wherein the catalyst is placed in tubes surrounded by a cooling medium such as boiling water, boiling Dowtherm ® (high-boiling heat transfer media) or flowing gas, or vice versa. Possibly an adiabactic and a cooled reactor may be combined according to similar principles as those described in U.S. patent application Ser. No. 99,361. Irrespective of which is utilized, the reaction may be operated with or without recycling of part of the product gas. Recycling limits the temperature increase. It is preferable to conduct the reaction in a fluidized catalyst bed with cooling.

The primary utility of the product gas is the utilization of the ethane and ethylene formed as a petrochemical raw material. Like propane, they may be sold as such or be subjected to steam cracking especially into ethylene. Part of the methane may be used as fuel for this, or it may be used as substitute natural gas or in another manner as fuel. When the synthesis is conducted with a $H_2/CO$ ratio close to 1:1, a considerable part of the product gas, about half thereof, is present as $CO_2$. This carbon dioxide must be removed if the hydrocarbons are to be separated. It should also be removed from the product gas if it is to be passed as a feed gas stream to a steam cracking plant which is used according to well-known principles for producing ethylene and small amounts of propylene. Carbon dioxide separated off may, if desired, be used as an oxidation agent in cases where the synthesis gas has been prepared from natural gas or liquid hydrocarbons. Methane and carbon dioxide separated from the product gas from the process according to the invention may optionally together be passed into a steam reformer and, together with more added methane and possibly the addition of steam, there be converted into synthesis gas for use as feed gas in the process of the invention.

If the ratio $H_2/CO$ of the synthesis gas is below 1, as is the case with some gases formed by the gasification of coal, the amount of hydrogen necessary for the ethanation may be brought to optimal levels by adding steam to the synthesis gas. Concurrently with the hydrocarbon/ethane reaction the catalyst will then cause the formation of the necessary hydrogen via the shift reaction (5).

The catalyst can be prepared according to well-known techniques. The support may, for instance, be formed by precipitation from a suitable solution of a salt of a suitable metal, e.g., titanium or titanium/aluminum, drying and optionally calcination, yet with care so that sintering is not caused to such a high degree that the pore volume becomes too small. Specific surface areas of the order of magnitude of 10 $m^2/g$ and above are desirable, especially 20–200, for instance, 30–100 $m^2/g$.

Before drying and calcination the support material is shaped into suitable bodies, for example, pellets, tablets or rings. The shaped bodies thereafter are impregnated with a solution, preferably aqueous solution of suitable compounds of the group V-B and/or VI-B metal and of the iron group metal, either successively or simultaneously, whereby the catalyst metals are deposited on the support as salts. Drying and calcination to convert the metals into oxides thereafter takes place. The bodies thus formed are ready for use, optionally after crushing of large bodies into irregular fragments.

The catalyst may also be prepared by the coprecipitation technique in which salts of the group V-B and/or VI-B metal and the iron group metal as well as salts of a suitable material for the carrier, e.g., aluminum salts such as aluminum nitrate, silicates, or particularly titanium salts or titanium dioxide are precipitated as hydroxides of, for instance, alkali or alkaline earth metal hydroxide or basic ammonium compounds. The precipitated material is filtered, washed and dried. A subsequent calcination sets the hydroxides into oxide form. The material is shaped into suitable bodies, e.g., granulate, tablets or rings. An after-calcination may optionally be carried out in order to increase the strength of the catalyst.

Whether the catalyst has been prepared by impregnation or coprecipitation it is ready for use but since the catalyst metals are present as oxide, they may, if desired, be presulphided to convert the oxides into sulphides (mono-, di-, poly-, and/or oxysulphides). This conversion may also be omitted since it automatically will take place when the catalyst is used according to its purpose in hydrocarbon syntheses in the presence of gaseous sulphur compounds.

The process and catalysts of the invention will be illustrated by the following non-limiting Examples.

EXAMPLE 1

Various catalysts were prepared in the following manner:

A ceramic support ($Al_2O_3$ or $TiO_2$) was impregnated with the desired metal salts in ammoniacal solution while adding about 2% by volume of alkanol amine to avoid precipitation of metal hydroxides. After air drying overnight this impregnated support was calcined by heating in air at 550° C. for 4 hours whereby salt residues were removed. Thereafter the metals were present on the catalyst as oxides. The catalysts were activated by sulphiding by heating under nitrogen at atmospheric pressure at 300° C. and replacing of the nitrogen stream with a stream of 2% hydrogen sulphide in hydrogen. Sulphiding can also take place during the beginning of the conversion reaction or, for instance, with carbon disulphide in hydrogen. The composition of the unused catalysts is set forth in Table 1, the support constituting the entire weight beyond catalyst metal and sulphur.

The testing of the catalysts was carried out with a synthesis gas consisting of 48% by volume $H_2$, 48% CO, 1% $H_2S$ and 3% Ar, the last-mentioned of which serves as an internal standard, e.g., for determining the gas concentration during synthesis. The temperature of the synthesis gas stream was 300° C., the pressure 30 bar. During the synthesis first and foremost reactions (5), (6), and (7) take place and of those the two last mentioned are presumed to be irreversible at temperatures below 500° C. and to take place via $CS_2$ and/or COS. Reaction (5) is reversible and faster than the hydrocarbon reactions.

The results are set forth in Table I. The standard activity is the amount of carbon monoxide that has reacted to form hydrocarbons, expressed as $NlC_1$/kg catalyst/hour, the amount of higher hydrocarbons having been calculated as the equivalent amount of methane and added to the amount of methane. The total conversion is the total amount of carbon monoxide which as been converted partly into hydrocarbons, partly into carbon dioxide, expressed in % of the initial amount of CO in the feed gas. The standard activity has moreover been calculated on the basis of the content of catalyst metal so that catalysts having different metal content can be compared directly. The Table also shows the space velocity (SV) in Nl synthesis gas per hour per kg catalyst; the total conversion of CO and the distribution of the hydrocarbons formed in the synthesis, wherein $C_n-$ means paraffins, $C_n=$ olefins, and na means not analyzed. The amount of the individual hydrocarbons has been stated in % by weight, calculated on the distribution of the carbon therein; accordingly, the figures show the amount of carbon converted into the hydrocarbon in question, expressed as proportion of the carbon of CO of the feed gas converted into hydrocarbons.

In the Table experiment No. 4 is in accordance with the invention whereas the remainder are not. The Table shows that the catalysts which are most selective for ethane are Mo/Co, Mo/Fe, Cr/Co, W/Co and V/Co and that the most active amongst these are those which contain Mo or V. As support materials $TiO_2$ clearly gives a higher activity than $Al_2O_3$ whereas they are equal with respect to selectivity.

Catalysts Nos. 8, 14, and 17 gave a small deposition of carbon (0.2–0.4%) on the catalysts, yet in such small amounts as to be insignificant.

TABLE I

| Exp. No. | Type | Catalyst composition, % by weight | | | Support | Standard activity $NlC_1$/h/kg | | SV Nl/ h/kg | Total conv. of CO, % | Distribution of carbon converted into hydrocarbons, % by weight | | | | | | | |
|---|---|---|---|---|---|---|---|---|---|---|---|---|---|---|---|---|---|
| | | | | | | Cat. | metal | | | $C_1$ | $C_2-$ | $C_2=$ | $C_3-$ | $C_3=$ | $C_4-$ | $C_4=$ | $C_5-$ |
| 1 | Mo/Co | 12.4 Mo | 1.1 Co | 5.9 S | $Al_2O_3$ | 62.4 | 460 | 1650 | 15.0 | 37 | 44 | | 16 | 3 | | | |
| 2 | | 13.9 Mo | 2.3 Co | 6.9 S | $Al_2O_3$ | 99.2 | 610 | 1650 | 23.8 | 27 | 48 | | 19 | | 5 | | 1 |
| 3 | Mo/Co | 6.6 Mo | 4.7 Co | 5.3 S | $Al_2O_3$ | 32.2 | 133 | 1200 | 11.2 | 16 | 47 | | 28 | | 7 | | 2 |
| 4 | Mo/Co | 6.8 Mo | 1.2 Co | 4.2 S | $TiO_2$ | 53.0 | 662 | 1700 | 13.4 | 32 | 48 | 1 | 15 | 1 | 3 | | |
| 5 | Mo/Fe | 11.5 Mo | 2.8 Fe | 5.9 S | $Al_2O_3$ | 54.5 | 380 | 1600 | 15.3 | 23 | 54 | | 19 | | 3 | | 1 |
| 6 | Cr/Co | 8.7 Cr | 2.9 Co | 2.0 S | $Al_2O_3$ | 7.9 | 68 | 7400 | 0.8 | 40 | 47 | 6 | 5 | 2 | | | |
| 7 | W/Co | 28.0 W | 2.2 Co | 2.9 S | $Al_2O_3$ | 3.5 | 55 | 970 | 6.1 | 26 | 52 | 1 | 18 | 1 | | | |
| 8 | V/Co | 5.9 V | 3.5 Co | 5.9 S | $Al_2O_3$ | 39.0 | 410 | 1900 | 9.3 | 23 | 48 | 1 | 21 | 1 | 5 | | 1 |
| 9 | V/Fe | | | | $Al_2O_3$ | 39.0 | | 1400 | 9.5 | 61 | 33 | 1 | 4 | | 1 | | |
| 10 | Mo | 12.5 Mo | | 4.1 S | $Al_2O_3$ | 149 | 845 | 3200 | 17.8 | 47 | 39 | | 12 | | 2 | | |
| 11 | Mo | 6.7 Mo | | 2.8 S | $TiO_2$ | 112 | 1670 | 3300 | 18.6 | 46 | 40 | 1 | 11 | 1 | 1 | | |
| 12 | Cr | | | | $Al_2O_3$ | 3.6 | | 3700 | 1.5 | 83 | 15 | 1 | 1 | | | | |
| 13 | W | 25.5 W | | 1.5 S | $Al_2O_3$ | 7.7 | 30 | 2300 | 2.7 | 85 | 1 | 8 | | 1 | 6 | | |
| 14 | V | 6.7 V | | 1.3 S | $Al_2O_3$ | 37.6 | 560 | 1900 | 11.3 | 76 | 21 | 1 | 2 | | 1 | | |
| 15 | Fe | | 3.4 Fe | 1.7 S | $Al_2O_3$ | 14.4 | 480 | 3400 | 2.4 | 48 | 39 | | 7 | | 7 | | |
| 16 | Co | | 3.0 Co | 1.0 S | $Al_2O_3$ | 7.2 | 240 | 3700 | 0.8 | 12 | 25 | 13 | 17 | 25 | 4 | 3 | 1 |
| 17 | Ni | | 5.8 Ni | 2.2 S | $Al_2O_3$ | 3.7 | 64 | 1300 | 2.0 | 24 | 18 | 2 | 24 | 7 | 26 | | |

EXAMPLE 2

The experiments of Example 1 were repeated with some selected catalysts in order to illustrate the influence of the temperature. The reaction conditions were as in Example 1, with the only exception that the temperature was varied. Table II shows that increased temperature favors the formation of methane at the cost of notably, $C_2$-hydrocarbons, and increases the activity.

TABLE II

| Catalyst No. | Temp., °C. | Activity Nl/h/kg metal | Carbon distribution (% by weight) of hydrocarbons | | | | | | | | |
|---|---|---|---|---|---|---|---|---|---|---|---|
| | | | $C_1$ | $C_2-$ | $C_2=$ | $C_3-$ | $C_3=$ | $C_4-$ | $C_4=$ | $C_5-$ | C |
| 2 | 300 | 610 | 27 | 48 | | 19 | | 5 | | 1 | |
|   | 489 | 4300 | 87 | 12 | | 1 | | | | | |
| 5 | 295 | 380 | 23 | 54 | | 19 | | 3 | | 1 | |
|   | 378 | 1470 | 37 | 47 | | 14 | | 2 | | | |
|   | 494 | 2590 | 85 | 14 | | 1 | | | | | |
| 8 | 300 | 410 | 23 | 48 | 1 | 21 | 1 | 5 | | 1 | |
|   | 403 | 3560 | 64 | 31 | 1 | 4 | | | | | |
|   | 501 | 7780 | 86 | 14 | | 1 | | | | | |

EXAMPLE 3

Increased pressure increases the selectivity for ethane and propane at the cost of methane, pentane and higher hydrocarbons as well as olefins. This is seen from Tables III and IV below, where the experiments were carried out almost as in Example 1, only with the exception that the pressures were varied. Table III shows the results with a catalyst where the ratio Mo to Co was 3.6 and the feed gas consisted of 49% $H_2$, 49% CO and 2% $H_2S$. The experiments in Table IV were carried out with the same feed gas as in Example 1 and with a catalyst containing 10.6% Mo, 2.0% Co and 0,08% K.

TABLE III

| Pressure, bar | Act. Nl/h/kg metal | Conv. % | $C_1$ % | $C_2-$ % | $C_2=$ % | $C_3-$ % | $C_3=$ % | $C_4-$ % | $C_4=$ % | $C_5-$ % |
|---|---|---|---|---|---|---|---|---|---|---|
| 30 | 8320 | 9.3 | 55 | 39 | 1 | 5 | na | na | na | na |
| 2 | 400 | 2.4 | 82 | 8 | 10 | na | na | na | na | na |

TABLE IV

| Pressure, bar | Act. Nl/h/kg metal | Conv. % | $C_1$ % | $C_2-$ % | $C_2=$ % | $C_3-$ % | $C_3=$ % | $C_4-$ % | $C_4=$ % | $C_5-$ % |
|---|---|---|---|---|---|---|---|---|---|---|
| 31.2 | 350 | 31.3 | 29 | 49 | — | 18 | 4 | 4 | — | 1 |
| 11.0 | 190 | 1.2 | 33 | 42 | 3 | 13 | 4 | 4 | — | 1 |
| 4.0 | 88 | 0.7 | 41 | 28 | 10 | 9 | 5 | 5 | — | 2 |
| 2.1 | 47 | 0.7 | 45 | 25 | 11 | 7 | 4 | 5 | — | 4 |

EXAMPLE 4

In experiments over a long period with a Mo/Co-catalyst (16% Mo, 3.2% Co) it was found that it maintained the activity reasonably well. The hydrocarbon distribution at integral conversion up to about 97% does not show a great difference from the distribution obtained at differential conditions, which partly is due to the fact that a certain concentrating of the gas takes place during the synthesis. The results of these experiments are shown in Table V below. The feed gas consisted of 48% $H_2$, 48% Co, 1% $H_2S$, 3% Ar (all % by vol.). The temperature was 300° C., the pressure varied as shown in the Table. The integral conditions have been underlined in the first column of the Table.

TABLE V

| Time, hours | Pressure, bar | Activity $NlC_1$/h/ kg metal | Total conv. of CO % | Hydrocarbon distribution (weight % C) | | | | | | | | SV Nl/h/ kg cat. |
|---|---|---|---|---|---|---|---|---|---|---|---|---|
| | | | | $C_1-$ | $C_2-$ | $C_2=$ | $C_3-$ | $C_3=$ | $C_4-$ | $C_4=$ | $C_5-$ | |
| 1 | 30.9 | 340 | 12.6 | 28 | 48 | | 19 | | 4 | | na | 2300 |
| 5.5 | 30.7 | — | 50.4 | 28 | 47 | | 16 | | 9 | | na | 130 |
| 30 | 30.2 | — | 73.0 | 31 | 47 | | 15 | | 7 | | | 130 |
| 30.5 | 29.9 | 250 | 9.4 | 26 | 47 | | 17 | | 10 | | | 2500 |
| 73 | 30.5 | — | 62 | 29 | 47 | | 16 | | 8 | | | 160 |
| 74 | 30.5 | 250 | 9.6 | 25 | 47 | | 17 | | 11 | | | 2200 |
| 117 | 29.5 | — | 84.7 | 36 | 46 | | 13 | | 5 | | | 70 |
| 150 | 34.6 | 230 | 9.4 | 26 | 51 | | 19 | | 4 | | 1 | 2100 |
| 151 | 64.0 | 330 | 14.4 | 24 | 51 | | 20 | | 5 | | 1 | 2000 |
| 170 | 64.0 | — | 96 | 32 | 49 | | 16 | | 3 | | | 125 |
| 194 | 64.7 | — | 97 | 32 | 47 | | 17 | | 3 | | 1 | 60 |
| 195 | 64.2 | 375 | 11.8 | 26 | 50 | | 19 | | 4 | | 1 | 2400 |
| 196 | 33.0 | 200 | 6.6 | 27 | 50 | | 19 | | 4 | | 1 | 2300 |

EXAMPLE V

In a similar manner as in Example 4 a V/Co catalyst (5.9% V, 3.5% Co) was tested at integral conditions. The duration of the experiment was almost 100 hours and the catalyst showed stable activity. In contradistinction to the experiment with the Mo/Co catalyst the proportion of hydrocarbons higher than methane increased from about 80 to about 89% at the integral conversion; the increase being mainly in the $C_3$-fraction.

The results are shown in Table VI which has been set up analogously to Table V, and the experiments were carried out with the same feed gas. The pressure was almost unvaried. port material is nevertheless higher than that of the alumina support.

TABLE VI

| Time, hours | Pressure, bar | Activity NlC$_1$/h/ kg metal | Total conv. of CO % | Hydrocarbon distribution (weight % C) | | | | | | | | SV Nl/h/ kg cat. |
|---|---|---|---|---|---|---|---|---|---|---|---|---|
| | | | | C$_1$— | C$_2$— | C$_2$= | C$_3$— | C$_3$= | C$_4$— | C$_4$= | C$_5$— | |
| 1.5 | 37.2 | 550 | 10 | 19 | 45 | 1 | 24 | 1 | 8 | | 2 | 2100 |
| 7 | 37.2 | — | 27 | 19 | 47 | | 25 | | 7 | | 1 | 550 |
| 69 | 37.5 | — | 49 | 12 | 44 | | 32 | | 10 | | 3 | 90 |
| 74 | 37.2 | 690 | 6.5 | 17 | 48 | 2 | 23 | 2 | 6 | | 2 | 4100 |
| 96 | 38.0 | — | 51 | 11 | 44 | | 32 | | 11 | | 3 | 80 |
| 97 | 37.0 | 500 | 3.6 | 21 | 47 | 2 | 19 | 3 | 4 | | 1 | 5100 |

EXAMPLE VI

Tests were conducted to compare the efficacy of titania and alumina as supports for the catalysts in the method of the invention.

Titania, alumina and titania/alumina supported catalysts employed in the test described hereinbelow were prepared according to the methods described in the above-entitled application, more particularly in Example I thereof.

Synthesis gas conversion employing the catalysts was conducted under the conditions set forth in Example I. A synthesis gas stream (48% H$_2$, 48% Co, 1% H$_2$S and 3% Ar, by volume) was passed at identical high space velocities over five different catalysts at 300° C. and a pressure of 30 bar.

The catalyst compositions, catalyst support materials and results of the tests are set forth in Table VII wherein:

The standard activity is the amount of carbon monoxide that has reacted to form hydrocarbons, expressed as NlC$_1$/kg catalyst/hour, the amount of higher hydrocarbons having been calculated as the equivalent amount of methane and added to the amount of methane. The standard activity was calculated on the basis of the content of catalyst metal so that catalysts having different metal content can be compared directly. The table also shows the distribution of the hydrocarbons formed in the synthesis. The amount of the individual hydrocarbons is stated in %C, by weight, calculated on the distribution of the carbon therein; accordingly, the figures show the amount of carbon converted into the hydrocarbon in question, expressed as proportion of the carbon content of CO in the feed gas converted into hydrocarbons.

Where the surface area of the titania support was increased (Cf. catalyst D), the activity increased to more than three times that of the alumina support, even though the surface area (135 sq. m/g) is not much more than one-half the surface area of catalyst A.

The supports of catalysts B and C have an activity about 65% greater than the alumina of catalyst A although their surface areas are about 16% and 55%, respectively, lower than the alumina support.

The tests were conducted utilizing high space velocities under laboratory conditions which are expected to yield low degrees of conversion. To determine the activity of alumina and titania supports under conditions more closely resembling industrial operations, catalysts A and E of Table VII were tested under the above-described conditions but at space velocities which cause 90% of the content of CO in the feed gas to be converted into hydrocarbons. Catalyst A resulted in a 90% conversion at a space velocity of 37 Nl/h/kg of catalyst whereas catalyst D resulted in a 90% converstion at a space velocity of 296 Nl/h/kg, thereby further evidencing the superiority of titania supports to alumina supports.

We claim:

1. In a process for the conversion of a synthesis gas mixture containing hydrogen and carbon oxides to a mixture of hydrocarbons by catalytic conversion, the improvement wherein said synthesis gas mixture contains at least 10 ppm of at least one gaseous sulfur compound calculated as H$_2$S and said conversion is conducted at a temperature of 270°–400° C. and at a pressure of 15–150 bar in the presence of a catalyst consisting of molybdenum sulfide and cobalt sulfide, said catalyst being supported on a porous oxidic support consisting essentially of titanium dioxide, whereby the pre-

TABLE VII

| Catalyst | Support | Weight Ratio titania alumina | Surface area m$^2$/g | Standard activity NlC$_1$/h/kg | | Catalyst Composition | | Distribution of carbon converted into hydrocarbons, % by weight | | | | |
|---|---|---|---|---|---|---|---|---|---|---|---|---|
| | | | | Cat. | Metal | Mo wt % | Co wt % | C$_1$ | C$_2$ | C$_3$ | C$_4$ | C$_5$ |
| A | Al$_2$O$_3$ | 0/100 | 230 | 99 | 610 | 13.9 | 2.3 | 27 | 48 | 19 | 5 | 1 |
| B | TiO$_2$/Al$_2$O$_3$ | 50/50 | 193 | 78 | 1050 | 6.1 | 1.3 | 28 | 52 | 14 | 2 | — |
| C | TiO$_2$/Al$_2$O$_3$ | 83/17 | 104 | 100 | 1070 | 7.6 | 1.8 | 26 | 51 | 18 | 3 | |
| D | TiO$_2$ | 100/0 | 135 | 180 | 2090 | 6.7 | 1.9 | 21 | 48 | 21 | 7 | 1 |
| E | TiO$_2$ | 100/0 | 32 | 53 | 662 | 6.8 | 1.2 | 32 | 49 | 16 | 3 | |

From the results set forth in Table VII it can be seen that, although the surface area of the alumina support (catalyst A), i.e., 230 sq. m/g is seven times greater than the surface area of the titania supported catalyst (catalyst E), i.e., 32 sq. m/g, the activity of the titania support material is nevertheless higher than that of the alumina support. dominant hydrocarbon component contained in said product mixture of hydrocarbons is a C$_2$-hydrocarbon.

2. A process as claimed in claim 1 wherein the conversion takes place at a temperaure of 300°–350° C. and a pressure of 20–100 bar.

* * * * *